(12) United States Patent
Ventouras

(10) Patent No.: US 6,183,775 B1
(45) Date of Patent: *Feb. 6, 2001

(54) BUCCAL DELIVERY SYSTEM

(75) Inventor: Kimon Ventouras, Carouge (CH)

(73) Assignee: Novartis Consumer Health S.A., Nyon (CH)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/180,242

(22) PCT Filed: May 6, 1997

(86) PCT No.: PCT/EP97/02299

§ 371 Date: Jan. 25, 1999

§ 102(e) Date: Jan. 25, 1999

(87) PCT Pub. No.: WO97/42941

PCT Pub. Date: Nov. 20, 1997

(30) Foreign Application Priority Data

May 13, 1996 (CH) .................................................. 96810303

(51) Int. Cl.⁷ .................................... A61K 9/20; A61K 9/22
(52) U.S. Cl. .......................... 424/465; 424/464; 424/468
(58) Field of Search .................................. 424/434, 464, 424/465, 468

(56) References Cited

U.S. PATENT DOCUMENTS

| | | | |
|---|---|---|---|
| 4,206,209 | 6/1980 | Kracauer | 424/234 |
| 4,806,356 | 2/1989 | Shaw et al. | 424/440 |
| 4,863,737 | 9/1989 | Stanley et al. | 424/440 |
| 4,967,773 | 11/1990 | Shaw | 131/359 |
| 5,288,497 | 2/1994 | Stanley et al. | 424/440 |
| 5,362,496 | 11/1994 | Baker et al. | 424/435 |
| 5,496,541 | * 3/1996 | Cutler | 424/50 |
| 5,549,906 | 8/1996 | Santus | 424/440 |

FOREIGN PATENT DOCUMENTS

| | | |
|---|---|---|
| 899037 | 6/1984 | (BE) . |
| 4333190 | 3/1995 | (DE) . |
| 0107941 | 5/1984 | (EP) . |
| 0142877 | 5/1985 | (EP) . |
| 0280571 | 8/1988 | (EP) . |
| 0290229 | 11/1988 | (EP) . |
| 0432956 | 6/1991 | (EP) . |
| 0601908 | 6/1994 | (EP) . |
| 2555901 | 6/1985 | (FR) . |
| 2255892 | 11/1992 | (GB) . |
| 9109599 | 7/1991 | (WO) . |
| 9503050 | 2/1995 | (WO) . |
| 9600070 | 1/1996 | (WO) . |

OTHER PUBLICATIONS

Amer. Pharm. Assoc. and Pharm. Soc. of Great Britain: "Handbook of Pharmaceutical Excipients", 1988, pp. 41–42; pp. 53–55; pp. 134–140.

* cited by examiner

Primary Examiner—Carlos A. Azpuru
(74) Attorney, Agent, or Firm—John D. Thallemer

(57) ABSTRACT

A controlled release lozenge having pleasant organoleptic properties, said lozenge consisting essentially of (a) a soluble filler which is selected from the group consisting of maltitol, xylitol, sorbitol, mannitol, lactose, dextrose, saccharose, fructose, and mixtures thereof; (b) an insoluble film forming agent which is capable of forming an insoluble matrix, said insoluble film forming agent is selected from the group consisting of a polyacrylate, ethyl cellulose, polyvinylchloride, cellulose acetate, cellulose acetate phthalate, and shellac; (c) a swellable polymer which is selected from the group consisting of xanthan gum, guar gum, alginic acid or a salt thereof, pectin, polyvinyl alcohol, polysaccharide, and cellulose derivatives; and (d) at least one active substance.

7 Claims, 1 Drawing Sheet

Release profiles of nicotine from different lozenges formulas following a "Suck-out test", in helthy volunteers mean value (n=6)

BUCCAL DELIVERY SYSTEM

CROSS REFERENCE TO RELATED APPLICATIONS

This application is a 35 U.S.C. 371 of PCT/EP97/0299, filed May 6, 1997.

The present invention relates to a slowly erodible lozenge having pleasant organoleptic properties, which means that the user has a pleasant feeling in the mouth when sucking it. When an active substance, especially a pharmaceutically active substance, is added to the composition, a buccal delivery system is obtained that releases the active substance slowly in a controlled manner, for example with almost zero order release.

The delivery of drugs through the buccal mucosa is a very well known and convenient way of administering a number of active ingredients for either local or systemic action. Chewable tablets, lozenges and other similar oral dosage forms have been present on the market for many years. These galenical forms often consist of a soluble diluent, such as sugar, lactose, mannitol or sorbitol, and a binder. Lubricants, flavours, sweetening agents, taste correctors and one or more active ingredients are normally added which do not improve the tableting properties of the mixture. These forms dissolve relatively rapidly once in the mouth, within either a few seconds or up to 10 minutes, and deliver both soluble and insoluble active ingredients to the buccal cavity.

Chewing gums are also present on the market. They are often used to increase the time over which the active ingredient is delivered to the buccal cavity—which can be up to more than a half an hour. However, these forms do also have their drawbacks, although they are popular and useful for several drugs, e.g. fluoride supplements, nicotine etc. One major drawback is that normally the taste changes rapidly in the mouth—often after only a few minutes of chewing—due to the rapid release of flavours and sweeteners occurring when the chewing action proceeds. Moreover, a chewing gum is not a discreet form of drug administration, and it can be unpleasant and tiring to chew for a long period of time several times a day.

SUMMARY OF THE INVENTION

The present invention relates to a new buccal delivery system which allows the delivery of a soluble or insoluble active substance to the buccal mucosa over an extended period of time. The delivery occurs in a controlled release manner normally within a period of from 15 minutes up to 90 minutes, or within an even longer period of time.

The buccal delivery system of the invention is in the form of a slowly erodible lozenge and consists essentially of (an insoluble matrix formed from)
(a) a soluble filler in an amount of from 50 up to 99 weight-% of the total composition,
(b) an insoluble film-forming agent which is capable of forming an insoluble matrix,
(c) a swellable polymer,
(d) optionally an active substance and
(e) optionally usual auxiliaries.

Figure 1:
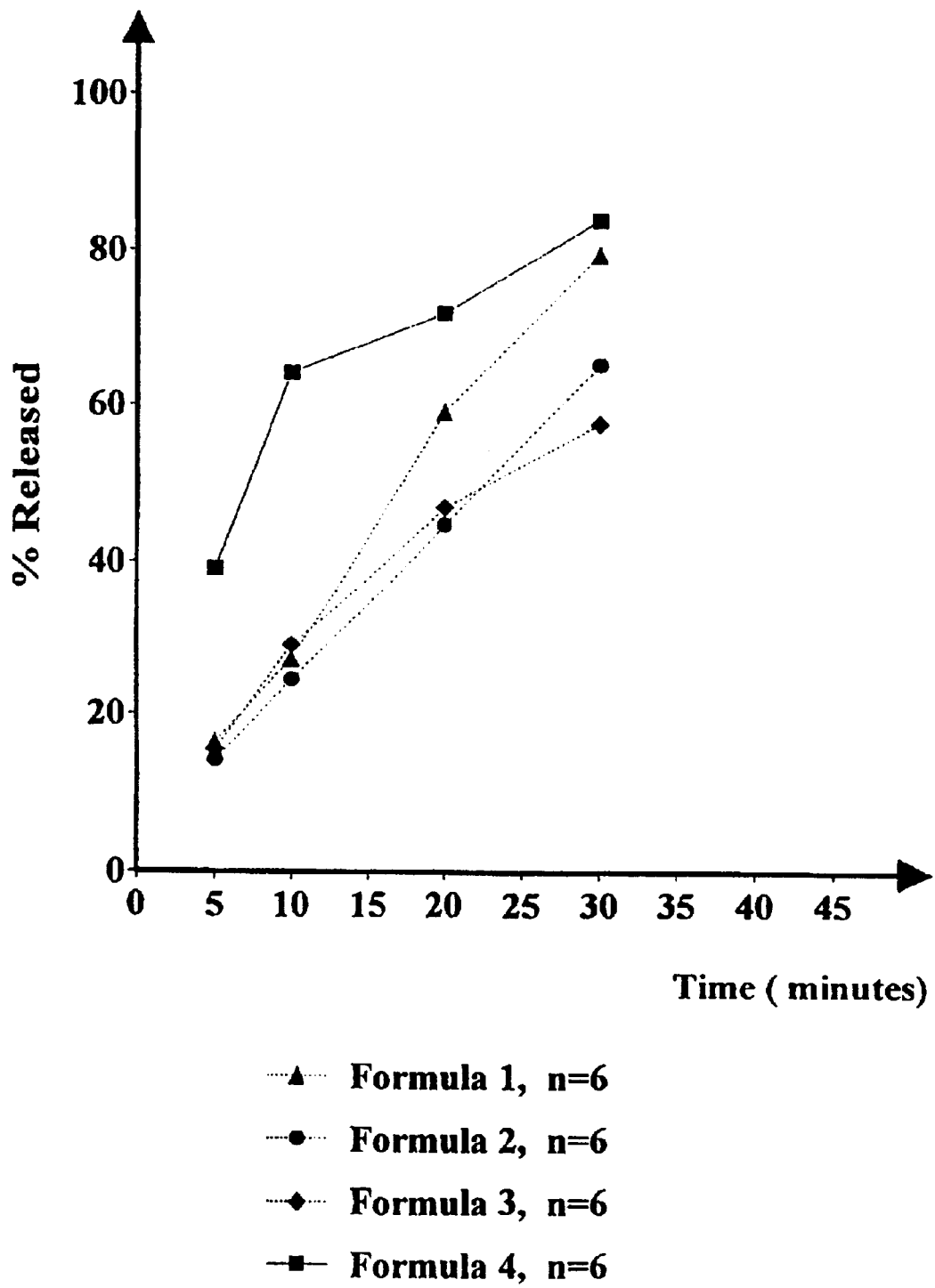
FIG. 1 is a graph which plots the percent of nicotine released vs. time (minutes) for four different lozenges.

As soluble filler (a) may be used, for example, any sugar or sugar-free sweetener, e.g. maltitol, xylitol, sorbitol, mannitol, lactose, dextrose, saccharose or fructose, or any mixture thereof, e.g. a mixture of xylitol and sorbitol, such as Xylisorb®. Preferred as soluble filler (a) is maltitol, xylitol, mannitol, dextrose or fructose, or any mixture thereof. Especially preferred as soluble filler (a) is maltitol, xylitol or mannitol, or any mixture thereof; in particular maltitol or xylitol, or any mixture thereof. Another embodiment of the preferred soluble fillers (a) consists of maltitol, xylitol, sorbitol or mannitol, or any mixture thereof.

The soluble filler (a) is preferably present in an amount of from 50 up to 95, more preferably in an amount of more than 55 up to 95, especially of from 60 up to 90, more especially of from 70 up to 90, and in particular of from 80 up to 90, weight-% of the total composition.

As insoluble film-forming agent which is capable of forming an insoluble matrix (b) may be used, for example, polyacrylates, which means homo- or co-polymers of alkyl esters, especially methyl and ethyl esters but also e.g. substituted alkyl esters such as dimethylaminoethyl esters, of acrylic acid and/or methacrylic acid, e.g. Eudragit® products such as Eudragit® S, Eudragit® NE, Eudragit® E or Eudragit® L of Roehm Pharma GmbH, Darmstadt (Germany). Further insoluble film-forming agents include e.g. ethyl cellulose, e.g. Aquacoat® products such as Aquacoat® ECD 30 of FMC Corp., Philadelphia (USA); polyvinylchloride, cellulose acetate, cellulose acetate phthalate or shellac. Mixtures of more than one of the mentioned substances can also be used as insoluble film-forming agent (b).

Preferred as insoluble film-forming agent (b) are polyacrylates, and especially such polyacrylates which are in the form of an aqueous dispersion, for example Eudragit® NE 30D.

The insoluble film-forming agent (b) is usually present in an amount of from 0.5 up to 30, especially of from 0.5 up to 24 and in particular of from 3 up to 10, weight-% of the total composition.

In the manufacture of the buccal delivery system of the invention, the insoluble film-forming agent which is capable of forming an insoluble matrix (b) may be applied e.g. as an aqueous dispersion (pseudolatex) or as a non-aqueous dispersion (using an organic solvent), or instead of dispersions as an aqueous or non-aqueous solution respectively, or in solid form.

To avoid any possible misunderstanding, the film-forming agent (b) is used here not as forming any film or coating but is intimately mixed with the other ingredients to form an insoluble matrix, i.e. the lozenge.

As swellable polymer (c) may be used any naturally occurring or synthetically obtained swellable polymer that is toxicologically acceptable. Examples for useful swellable polymers are xanthan gum, guar gum, alginic acid or a salt thereof, such as sodium alginate, pectins, polyvinyl alcohol, polysaccharides, e.g. dextrans, and swellable cellulose derivatives such as sodium or calcium carboxymethylcellulose, , e.g. from the Methocel® series of Dow Chem., Midland (USA), hydroxyethylcellulose, e.g. Klucel®, or hydroxypropylcellulose. Mixtures of more than one of the mentioned substances can also be used as swellable polymer (c).

Preferred swellable polymers (c) are xanthan gum, guar gum, alginic acid or a salt thereof, such as sodium alginate, and swellable cellulose derivatives such as sodium or calcium carboxymethylcellulose, hydroxypropylmethylcellulose, hydroxyethylcellulose or hydroxypropylcellulose.

Especially preferred as swellable polymer (c) is xanthan gum.

The swellable polymer (c) is usually present in an amount of from 0.5 up to 30, especially of from 0.5 up to 24 and in particular of from 3 up to 10, weight-% of the total composition.

The active substance (d) is, for example, a pharmaceutically active substance. It may be from any class of pharmaceutically active substances that can be administered orally or through the buccal mucosa, respectively. Pharmaceutically active substances are also to be understood as to include e.g. nicotine and salts and derivatives thereof as an aid for smoking cessation. Classes of pharmaceutically active substances that come into consideration are, for example, nicotine and salts and derivatives thereof, e.g. nicotine tartrate or nicotine polacrilex (=resin complex containing nicotine, e.g. 10 or 20 weight-% of nicotine), in particular nicotine tartrate; hormones, e.g. melatonin; fluoride supplements, e.g. sodium fluoride or others fluoride salts; local disinfectants, e.g. benzoxonium chloride, chlorhexidine or benzalkonium chloride; local anaesthetic agents, e.g. lidocaine, benzocaine, novocaine or nupercaine; analgesic and/or antiinflammatory agents, e.g. acetylsalicylic acid, diclotenac, paracetamol or ibuprofen; antacids; antiemetics; agents against dental plaque; agents against aphthae; $H_2$-receptor antagonists, e.g. ranitidine or cimetidine; preparations containing bacteria, especially bacteria selected from the genus lactobacillus and/or bifidobacterium; antibiotics, anorexics, antiasthmatics, antidiuretics, antimigraine agents, antispasmodics, sedatives, antihyperactives, tranquilizers, antihistamines, decongestants, betablockers, and combinations thereof.

Usual auxiliaries that are optionally present (e) are known in the art and include lubricants, flavors, aromas, sweeteners, colorants, buffering agents, acidifying agents, diluents, preservatives, glidants, e.g. colloidal silicium dioxide, and the like.

The buccal delivery system of the invention permits the controlled erosion of the lozenge in the mouth due to the effects of sucking, without any break-up of the lozenge, together with pleasant organoleptic properties and close to zero order release of the active ingredient. "Zero order release" means that the time-release relationship is linear (see FIG. 1).

It a buccal delivery system is manufactured only from a mixture of the soluble filler (a) with the insoluble film-forming agent (b)—under omission of the swellable polymer (c)—, lozenges are obtained that have prolonged release properties but also unpleasant organoleptic properties. Especially during the sucking process, the insoluble film-forming agent remains in the mouth as an insoluble filament which has an unpleasant taste and consistency.

If a buccal delivery system is manufactured only from a mixture of the soluble filler (a) with the swellable polymer (c)—under omission of the insoluble film-forming agent (b)—, by compression, lozenges are obtained that have prolonged release properties but that cause an unpleasant sensation of swelling and gelling in the mouth. Moreover, these lozenges are easily breakable in the mouth and are highly affected by sucking which often becomes evident within the first 10 minutes after taking the lozenge.

In contrast, when sucking the lozenges of the invention, the swellable polymer (c) swells only on the surface of the wet lozenge. Small pieces of the swellable polymer (=gelling agent) (c) are eroded from the surface of the lozenge together with the insoluble film-forming agent (b). The mixture of eroded particles (c) and (b) is not perceptible in the mouth. The size of the erodible lozenge is diminished but its shape remains unchanged until the end of the sucking process. In other words, the erodible lozenge does not break until—in the end—it is completely eroded and dissolved. Moreover, as mentioned earlier, the release from the lozenge is almost constant (zero order release). These findings were confirmed in sucking tests that were performed in healthy volunteers (see FIG. 1, especially formulae 1 and 2).

The new oral swellable dosage form of the invention can be formulated to be more or less slowly erodible in the mouth according to the desired release profile (cp. FIG. 1, formulae 1 and 2). A more slowly erodible lozenge is obtained, if the amount of the insoluble film-forming agent (b), e.g. a polyacrylate dispersion, and/or the amount of the swellable polymer (c), e.g. xanthane gum, is increased.

Thus, surprisingly, it was found that the mixture of the three essential components (a), (b) and (c) results in controlled release lozenges (1) with an improved delayed release by erosion and diffusion, (2) with almost zero order release (see FIG. 1, formulae 1 and 2), and (3) with pleasant organoleptic properties.

The slowly erodible lozenges of the present invention must not be confused with hard candies (like "bonbons"), which are hard, do not swell and usually contain liquefied sugars like corn syrup.

The buccal delivery system of the invention can be manufactured by several different manufacturing methods, for example, by (1) a traditional wet granulation process incorporating all ingredients, and subsequent compression, or
(2) a two stage process consisting of a granulation stage of only some of the ingredients, which is followed by the addition of the other ingredients, e.g. the active substance, in the external phase (see Formulae 1, 2, 3 and 5), and subsequent compression, or
(3) a direct compression process without a granulation stage (see Formula 4).

All methods mentioned have in common a final compression step. Thus, the lozenges of the present invention are preferably obtained—in principle—by compression of a mixture of the components (a), (b), (c), (d) and (e).

The following examples illustrate the invention but do not limit it in any way.

| Formula 1: Composition (for 1000 lozenges): | |
|---|---|
| Nicotine tartrate dihydrate | 3.07 g |
| Maltitol | 880.0 g |
| Sodium bicarbonate | 20.0 g |
| Polyacrylate dispersion 30% | 50.0 g (dry mass) |
| Xanthane gum | 40.0 g |
| Colloidal anhydrous silica | 15.0 g |
| Magnesium stearate | 20.0 g |

Manufacturing Method

In a fluid bed mix the maltitol, sodium carbonate and ⅔ of the colloidal anhydrous silica. Granulate this mixture with the polyacrylate dispersion using a contra-current fluid bed granulation. Mix the dry granules with the nicotine tartrate, xanthane gum, the remaining ⅓ of the colloidal anhydrous silica and the magnesium stearate. Compress this mixture to produce 15 mm biconvex round lozenges with a mass of about 1028 mg.

| Formula 2: Composition (for 1000 lozenges): | |
| --- | --- |
| Nicotine tartrate dihydrate | 3.07 g |
| Maltitol | 880.0 g |
| Sodium carbonate anhydrous | 40.0 g |
| Polyacrylate dispersion 30% | 70.0 g (dry mass) |
| Xanthane gum | 60.0 g |
| Colloidal anhydrous silica | 15.0 g |
| Peppermint | 30.0 g |
| Levomenthol | 3.0 g |
| Saccharine sodium | 5.0 g |
| Magnesium stearate | 20.0 g |

Manufacturing Method

In a fluid bed mix the maltitol, sodium carbonate anhydrous, and ⅔ of the colloidal anhydrous silica. Granulate this mixture with the polyacrylate dispersion using a contra-current fluid bed granulation. Mix the dry granules with the nicotine tartrate, xanthane gum, the remaining ⅓ of the colloidal anhydrous silica, the levomenthol, peppermint, saccharine sodium and the magnesium stearate. Compress this mixture to produce 15 mm biconvex round lozenges with a mass of about 1126 mg.

| Formula 3: Composition (for 1000 lozenges): | |
| --- | --- |
| Nicotine tartrate dihydrate | 3.07 g |
| Xylitol | 880.0 g |
| Sodium carbonate anhydrous | 40.0 g |
| Polyacrylate dispersion 30% | 50.0 g (dry mass) |
| Xanthane gum | 40.0 g |
| Colloidal anhydrous silica | 15.0 g |
| Cinnamon flavour | 15.0 g |
| Saccharine sodium | 5.0 g |
| Magnesium stearate | 20.0 g |

Manufacturing Method

In a fluid bed mix the maltitol, sodium carbonate anhydrous, and ⅔ of the colloidal anhydrous silica. Granulate this mixture with the polyacrylate dispersion using a contra-current fluid bed granulation. Mix the dry granules with the nicotine tartrate, xanthane gum, the remaining ⅓ of colloidal anhydrous silica, the levomenthol, peppermint, saccharine sodium and the magnesium stearate. Compress this mixture to produce 15 mm biconvex round lozenges with a mass of about 1068 mg.

| Formula 4: Composition (for 1000 lozenges): | |
| --- | --- |
| Nicotine tartrate dihydrate | 3.07 g |
| Xylisorb ® (=mixture of xylitol and sorbitol) | 850.0 g |
| Sodium carbonate anhydrous | 40.0 g |
| Eudragit S-100 ® | 100.0 g |
| Xanthane gum | 40.0 g |
| Colloidal anhydrous silica | 5.0 g |
| Peppermint | 30.0 g |
| Levomenthol | 3.0 g |
| Saccharine sodium | 5.0 g |
| Magnesium stearate | 20.0 g |

Manufacturing Method

Mix all the ingredients together, except for the magnesium stearate, and screen through a Frewitt fitted with a screen of 0.63 mm aperture size. Add the magnesium stearate and mix for 5 minutes. Compress this mixture to produce 15 mm biconvex round lozenges with a mass of about 1096 mg.

| Formula 5: Composition (for 1000 lozenges): | |
| --- | --- |
| Nicotine tartrate dihydrate | 3.07 g |
| Maltitol | 880.0 g |
| Sodium carbonate | 10.0 g |
| Sodium bicarbonate | 20.0 g |
| Polyacrylate dispersion 30% | 50.0 g (dry mass) |
| Xanthane gum | 40.0 g |
| Colloidal anhydrous silica | 15.0 g |
| Levomenthol | 3.0 g |
| Peppermint oil | 5.0 g |
| Aspartame | 10.0 g |
| Magnesium stearate | 20.0 g |

Manufacturing Method

In a fluid bed mix the maltitol, sodium carbonate, sodium bicarbonate and ⅔ of the colloidal anhydrous silica. Granulate this mixture with the polyacrylate dispersion using a contra-current fluid bed granulation. Mix the dry granules with the nicotine tartrate, xanthane gum, the remaining ⅓ of the colloidal anhydrous silica, the magnesium stearate, levomenthol, peppermint oil, and aspartame. Compress this mixture to produce 15 mm biconvex round lozenges with a mass of about 1056 mg.

What is claimed is:

1. A controlled release lozenge having pleasant organoleptic properties, said lozenge consisting essentially of
   (a) 50 to 99 weight percent, based on the total weight of the lozenge, of a soluble filler which is selected from the group consisting of maltitol, xylitol, sorbitol, mannitol, lactose, dextrose, saccharose, fructose, and mixtures thereof;
   (b) 0.5 to 30 weight percent, based on the total weight of the lozenge, of an insoluble film forming agent which is capable of forming an insoluble matrix, said insoluble film forming agent is selected from the group consisting of a polyacrylate, ethyl cellulose, polyvinylchloride, cellulose acetate, cellulose acetate phthalate, shellac, and mixtures thereof;
   (c) 0.5 to 30 weight percent, based on the total weight of the lozenge, of a swellable polymer which is selected from the group consisting of xanthan gum, guar gum, alginic acid or a salt thereof, pectin, polyvinyl alcohol, polysaccharide, cellulose derivatives, and mixtures thereof; and
   (d) at least one active substance.

2. A controlled release lozenge having pleasant organoleptic properties, said lozenge consisting essentially of
   (a) 55 to 95 weight percent, based on the total weight of the lozenge, of a soluble filler which is selected from the group consisting of maltitol, xylitol, sorbitol, mannitol, lactose, dextrose, saccharose, fructose, and mixtures thereof;
   (b) 0.5 to 24 weight percent, based on the total weight of the lozenge, of an insoluble film forming agent which is capable of forming an insoluble matrix, said insoluble film forming agent is selected from the group consisting of a polyacrylate, ethyl cellulose, polyvinylchloride, cellulose acetate, cellulose acetate phthalate, shellac, and mixtures thereof;
   (c) 0.5 to 24 weight percent, based on the total weight of the lozenge, of a swellable polymer which is selected from the group consisting of xanthan gum, guar gum, alginic acid or a salt thereof, pectin, polyvinyl alcohol, polysaccharide, and cellulose derivatives; and (d) at least one active substance.

3. The lozenge according to claim 1 wherein the active ingredient is nicotine or a salt or derivative of nicotine.

4. The lozenge according to claim 3 wherein the active ingredient is nicotine tartrate.

5. The lozenge according to claim 1 which additionally contains an auxiliary.

6. The lozenge according to claim 1 wherein the active substance is selected from the group consisting of a fluoride supplement, melatonin, a mixture of benzoxonium chloride and lidocaine, an antacid, an antiemetic, an analgesic agent, an agent against dental plaque, and combinations thereof.

7. The lozenge according to claim 1 wherein the release of the active substance is substantially in a constant manner.

* * * * *

UNITED STATES PATENT AND TRADEMARK OFFICE
CERTIFICATE OF CORRECTION

PATENT NO. : 6,183,775 B1
DATED : February 6, 2001
INVENTOR(S) : Kimon Ventouras It is certified that error appears in the above-identified patent and that said Letters Patent is hereby corrected as shown below:

<u>Title page,</u>
Please list as follows:

-- [30] Foreign Application Priority Data
May 13, 1996 (DE) ............................ 96810303 --

Item [56], under FOREIGN PATENT DOCUMENTS, add:

-- 0381182    8/1990    (EP). --

<u>Column 6,</u>
Last line, after "derivatives", insert -- , and mixtures thereof --

Signed and Sealed this

Nineteenth Day of March, 2002

Attest:

JAMES E. ROGAN
Attesting Officer
Director of the United States Patent and Trademark Office